US007966891B2

(12) United States Patent
Li et al.

(10) Patent No.: US 7,966,891 B2
(45) Date of Patent: Jun. 28, 2011

(54) FATIGUE TEST APPARATUS FOR THIN ELEMENT OF ELECTRONIC DEVICE

(75) Inventors: Lei Li, Shenzhen (CN); Ping Chen, Shenzhen (CN); Zhi-Qiang Jiang, Shenzhen (CN); Chun-Ying Wang, Shenzhen (CN); Xue-Liang Zhai, Shenzhen (CN); Li-Ping Huang, Shenzhen (CN); Zhi Cheng, Shenzhen (CN); Chang-Fa Sun, Shenzhen (CN); Xian-Cui Du, Shenzhen (CN)

(73) Assignees: Shenzhen Futaigong Precision Industry Co., Ltd., Shenzhen, Guangdong Province (CN); FIH (Hong Kong) Limited, Kowloon (HK)

( * ) Notice: Subject to any disclaimer, the term of this patent is extended or adjusted under 35 U.S.C. 154(b) by 274 days.

(21) Appl. No.: 12/417,764

(22) Filed: Apr. 3, 2009

(65) Prior Publication Data
US 2009/0260451 A1   Oct. 22, 2009

(30) Foreign Application Priority Data

Apr. 22, 2008   (CN) .......................... 2008 1 0301248

(51) Int. Cl.
*G01N 3/20*   (2006.01)

(52) U.S. Cl. ......................................................... 73/852
(58) Field of Classification Search .................... 73/852, 73/856
See application file for complete search history.

(56) References Cited

U.S. PATENT DOCUMENTS

| 2,317,097 | A | * | 4/1943 | Eksergian | ........................ | 73/666 |
| 5,693,890 | A | * | 12/1997 | Holmes | ........................... | 73/856 |
| 6,145,390 | A | * | 11/2000 | Jahn et al. | ..................... | 73/865.5 |
| 7,757,566 | B2 | * | 7/2010 | Li et al. | ........................... | 73/810 |
| 2009/0292498 | A1 | * | 11/2009 | Li et al. | ........................... | 702/117 |

* cited by examiner

*Primary Examiner* — Lisa M. Caputo
*Assistant Examiner* — Octavia Davis
(74) *Attorney, Agent, or Firm* — Steven M. Reiss

(57) ABSTRACT

A fatigue test apparatus for thin workpiece includes a supporting module, a driving mechanism, a first connecting module, a second connecting module, a first holding post, a second holding post and a computer system. The first and second connecting modules are respectively fixed to two sides of the supporting module. Ends of the first holding post and the second holding post are fixed to the first and second connecting modules. The computer system electronically connects with and controls the driving mechanism. The first holding post and the second holding post are drive to rotate by the driving mechanism.

20 Claims, 3 Drawing Sheets

US 7,966,891 B2

FATIGUE TEST APPARATUS FOR THIN ELEMENT OF ELECTRONIC DEVICE

BACKGROUND

1. Technical Field

The present invention relates to fatigue test apparatus, particularly, to a fatigue test apparatus for thin elements of electronic devices.

2. Description of Related Art

In industrial production of electronic devices, it is often necessary to test fatigue strength of some elements (e.g., antenna, flexible circuit board) of the electronic devices, to ensure the quality of the products. In conventional fatigue test for these elements, a fixing device is generally used to hold an element, and the element undergoes repeated bending by an operator until it breaks. However, in conventional fatigue test, the labor intensity of the operator is heavy. In addition, since the operator is unlikely to apply a same force to the element at every time, the result of the fatigue test may be inaccurate.

Therefore, there is space for improvement within the art.

BRIEF DESCRIPTION OF THE DRAWINGS

Many aspects of the fatigue test apparatus can be better understood with reference to the following drawings. The components in the drawings are not necessarily drawn to scale, the emphasis instead being placed upon clearly illustrating the principles of the present fatigue test apparatus, in which.

DETAILED DESCRIPTION OF THE EMBODIMENTS

Figure 1:
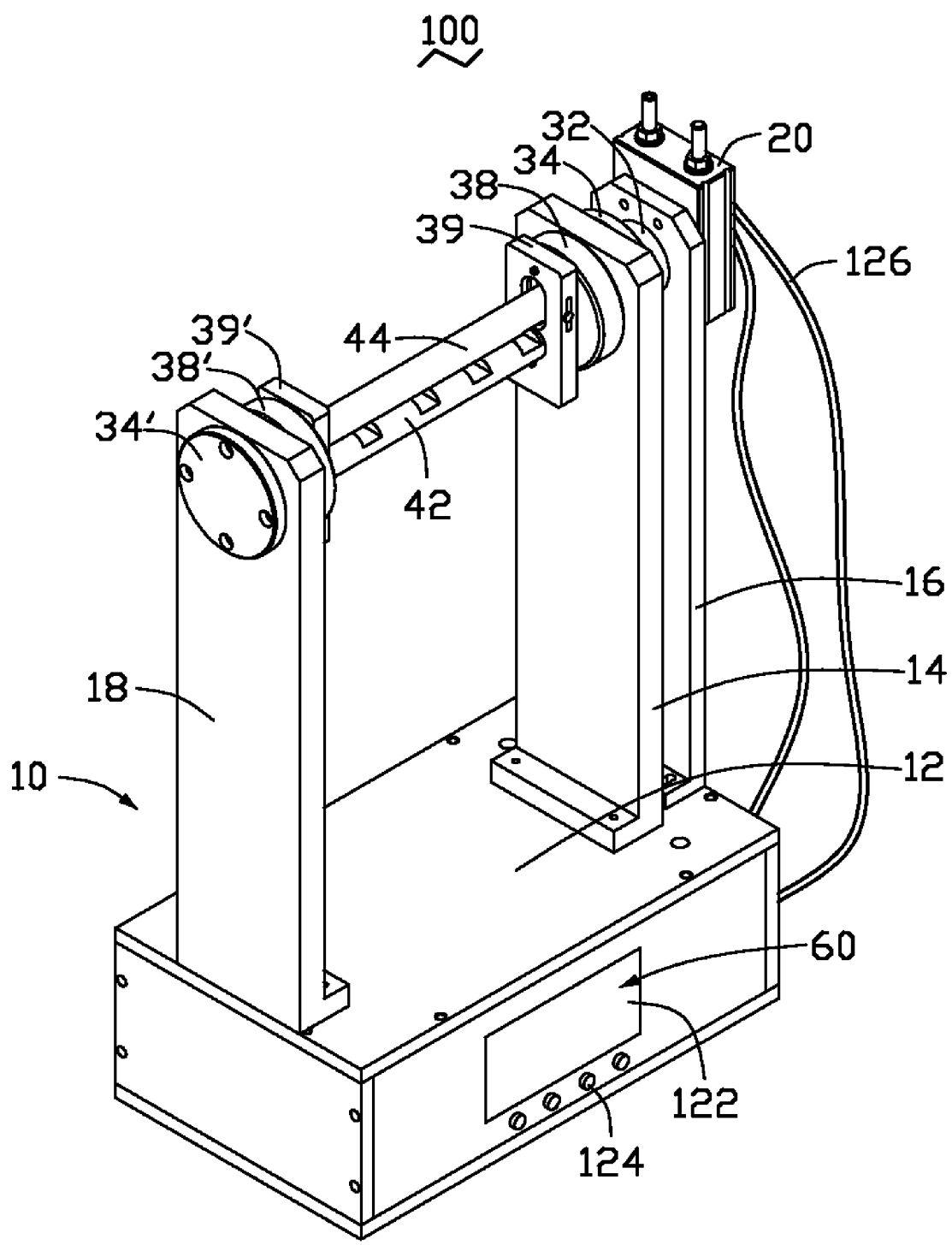
FIG. 1 is an assembled, schematic view of a fatigue test apparatus, in accordance with an exemplary embodiment.
Figure 2:
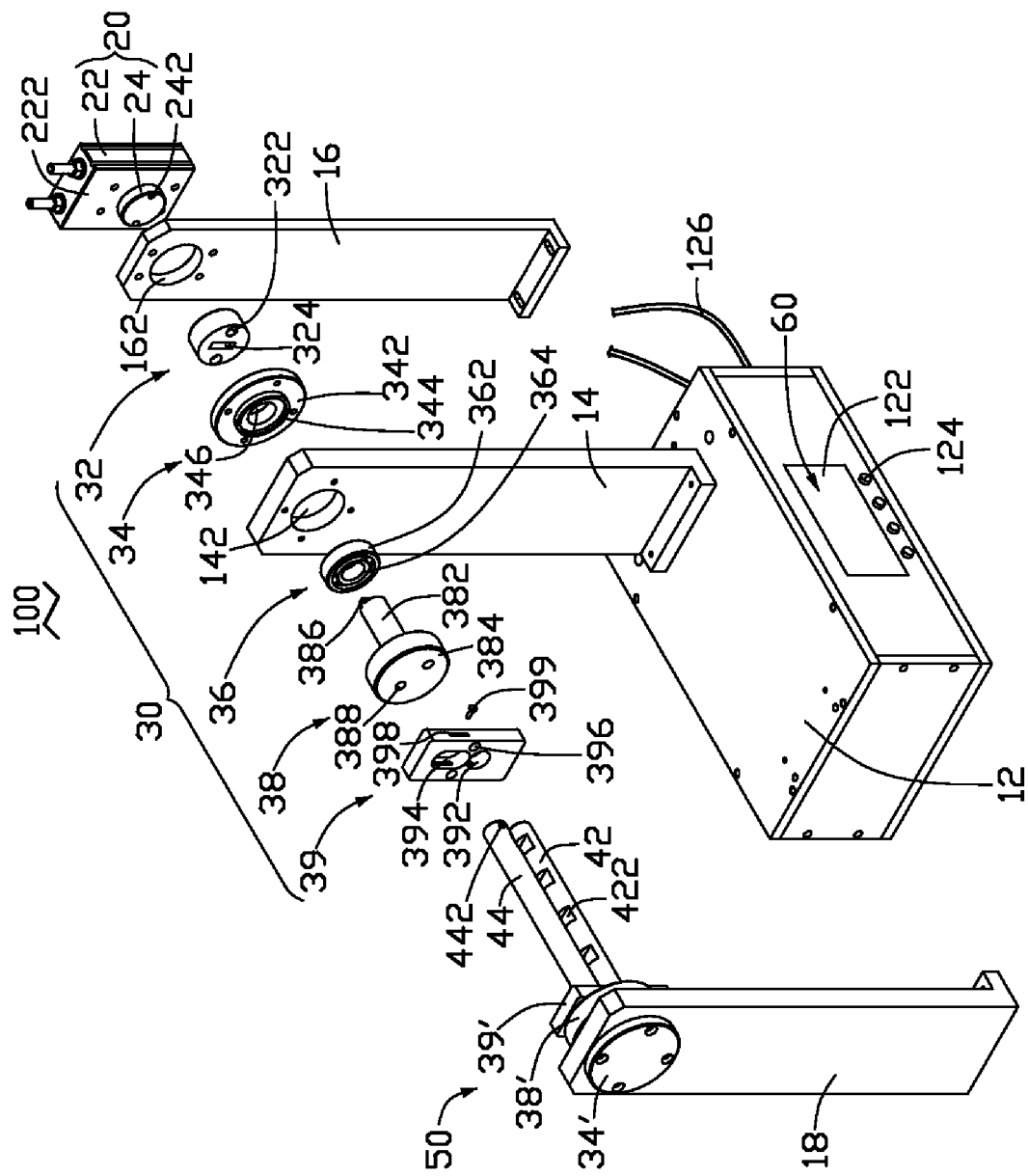
FIG. 2 is an exploded, schematic view of the fatigue test apparatus shown in FIG. 1.

Referring to FIGS. 1-2, a fatigue test apparatus 100 in accordance with an exemplary embodiment includes a supporting module 10, a driving mechanism 20, a first connecting module 30, a first holding post 42, a second holding post 44, a second connecting module 50, a computer system 60.

The supporting module 10 includes a base 12, a first supporting arm 14, a second supporting arm 16, and a third supporting arm 18. The base 12 is box-shaped, and receives the computer system 60 therein. A display 122 and a plurality of buttons 124 are located on a sidewall of the base 12. The display 122 and buttons 124 electronically connect with the computer system 60. The supporting arms 14, 16 and 18 are fixed on a top surface of the base 12 spaced apart from each other. The distance between the third supporting arm 18 and the first supporting arm 14 is longer than that of the first supporting arm 14 and the second supporting arm 16. Each of the first and third supporting arms 14, 18 defines a through hole 142 at it free end. The second supporting arm 16 has a fixing hole 162 at its free end. The two through holes 142 and the fixing hole 162 are coaxial.

The driving mechanism 20 includes a rotary cylinder and a cylinder block 22. The cylinder block 22 has a sidewall 222. A drive shaft 24 extends out from the sidewall 222 of the cylinder block 22. The drive shaft 24 is configured for engaging with the fixing hole 162 of the second supporting arm 16, and has two first connecting holes 242 defined in one end thereof.

The first connecting module 30 includes a connecting shaft 32, a first cover 34, a bearing 36, a first connecting member 38 and a first swing block 39. The connecting shaft 32 is column-shaped, and defines two first receiving holes 322 and a locking slot 324. The connecting shaft 32 can connect with the drive shaft 24 by inserting a pin into each pair of the first connecting hole 242 and the first receiving hole 322. The locking slot 324 has a rectangular cross-section.

The first cover 34 is disc-shaped, and includes a main body 342 and a circular flange 344 extending from the main body 342. The main body 342 defines a shaft hole 346 in a middle area thereof. The shaft hole 346 and the circular flange 344 are coaxial. An outer diameter of the circular flange 344 is configured for matching the through hole 142 of the first supporting arm 14.

The bearing 36 has an outer circumferential surface 362 and an inner circumferential surface 364. A diameter of the outer circumferential surface 362 is configured for matching the through hole 142 of the first supporting arm 14.

The first connecting member 38 includes a shaft portion 382 and a flange head 384 at one end of the shaft portion 382. A diameter of the shaft portion 382 is configured for matching the inner circumferential surface 364 of the bearing 36 and the haft hole 346 of the first cover 34. A rectangular protrusion 386 is formed at another end of the shaft portion 382, configured for being locked in the locking slot 324 of the connecting shaft 32. The flange head 384 defines two second connecting holes 388 at an opposite side of the shaft portion 382.

The first swing block 39 is rectangular, and defines a holding hole 392, a sliding groove 394 and two second receiving holes 396. The holding hole 392 is configured for securing one end of the first holding post 42. The sliding groove 394 has a width similar than a diameter of the second holding post 44. The length of the sliding groove 394 is double the width of the sliding groove 394. The first swing block 39 can be connected with the first connecting member 38 by inserting a pin into a pair of the second connecting hole 388 and the second receiving hole 396. The first swing block 39 defines a locking screw hole 398 in a sidewall thereof, configured for matching with a screw 399. The locking screw hole 398 is perpendicular to and communicates to the sliding groove 394.

The two holding posts 42, 44 are generally column-shaped. Each holding posts 42, 44 defines a plurality of recesses 422 in a circumferential surface thereof. Each pair of corresponding recesses 422 of the first and second holding posts 42,44 are configured for receiving a workpiece (e.g., antenna or flexible circular board). The second holding post 44 defines a positioning hole 442 at each end thereof. The positioning holes 442 are screw holes, matching the screw 399. The position of the second holding post 44 can be adjusted by positioning the screw 399 at different positions of the locking screw hole 398.

The second connecting module 50 includes a second cover 34', a bearing (not shown), a second connecting member 38' and a second swing block 39'. The configuration of the second cover 34', second connecting member 38' and second swing block 39' are respectively slightly different from that of the first cover 34, the first connecting member 38 and the first swing block 39. A shaft hole (not shown) of the second cover 34' is a blind hole. A shaft portion (not shown) of the second connecting member 38' is shorter than the shaft portion 382 of the first connecting member 38, and does not have a protrusion formed at one end thereof.

The computer system 60 electronically connects with the driving mechanism 20 by wires 126. The rotation angle and rotation speed of the drive shaft 24 can be predetermined by operating the buttons 124 which electronically connects with the computer system 60. During tests, the amount of time that the drive shaft 24 has rotated can be shown in the display 122 in time.

In assembly of the fatigue test apparatus 100, the driving mechanism 20 is fixed to the second supporting arm 16 by screws, with the drive shaft 24 received in the fixing hole 162 and facing the first supporting arm 14. The connecting shaft 32 is attached to the drive shaft 24 by inserting pins into the first connecting holes 242 and first receiving holes 322. The first cover 34 is fixed to the first supporting arm 14 by screws, with the circular flange 344 received in the through hole 142 of the first supporting arm 14. The bearing 36 is inserted into the through hole 142 of the first supporting arm 14. Two sides of first cover 34 respectively resist the connecting shaft 32 and the circular flange 344 of the first cover 34. The shaft portion 382 of the first connecting member 38 passes the bearing 36, the shaft hole 346 of the first cover 34, and then the protrusion 386 engages in the locking slot 324 of the connecting shaft 32. The flange head 384 of the first connecting member 38 resists the first supporting arm 14.

The second cover 34' is attached to the third supporting arm 18 by screw. The bearing 36 and the second connecting member 38' are then assembled to the third supporting arm 18 in order.

Two ends of the first holding post 42 are respectively inserted into the holding holes 392 of the first and second swing blocks 39,39'. Two ends of the second holding post 44 are respectively inserted into the sliding grooves 394 of the first and second swing blocks 39,39'. Two screws 399 are respectively rotated into the sliding grooves 394. The first and second swing blocks 39,39' are respectively attached to the flange heads 384 of the first and second connecting members 38,38' by inserting pins into the second connecting holes 388 and the second receiving holes 396. At last, the driving mechanism 20 is electronically connected with the computer system 60 by the two wires 126.

Figure 3:
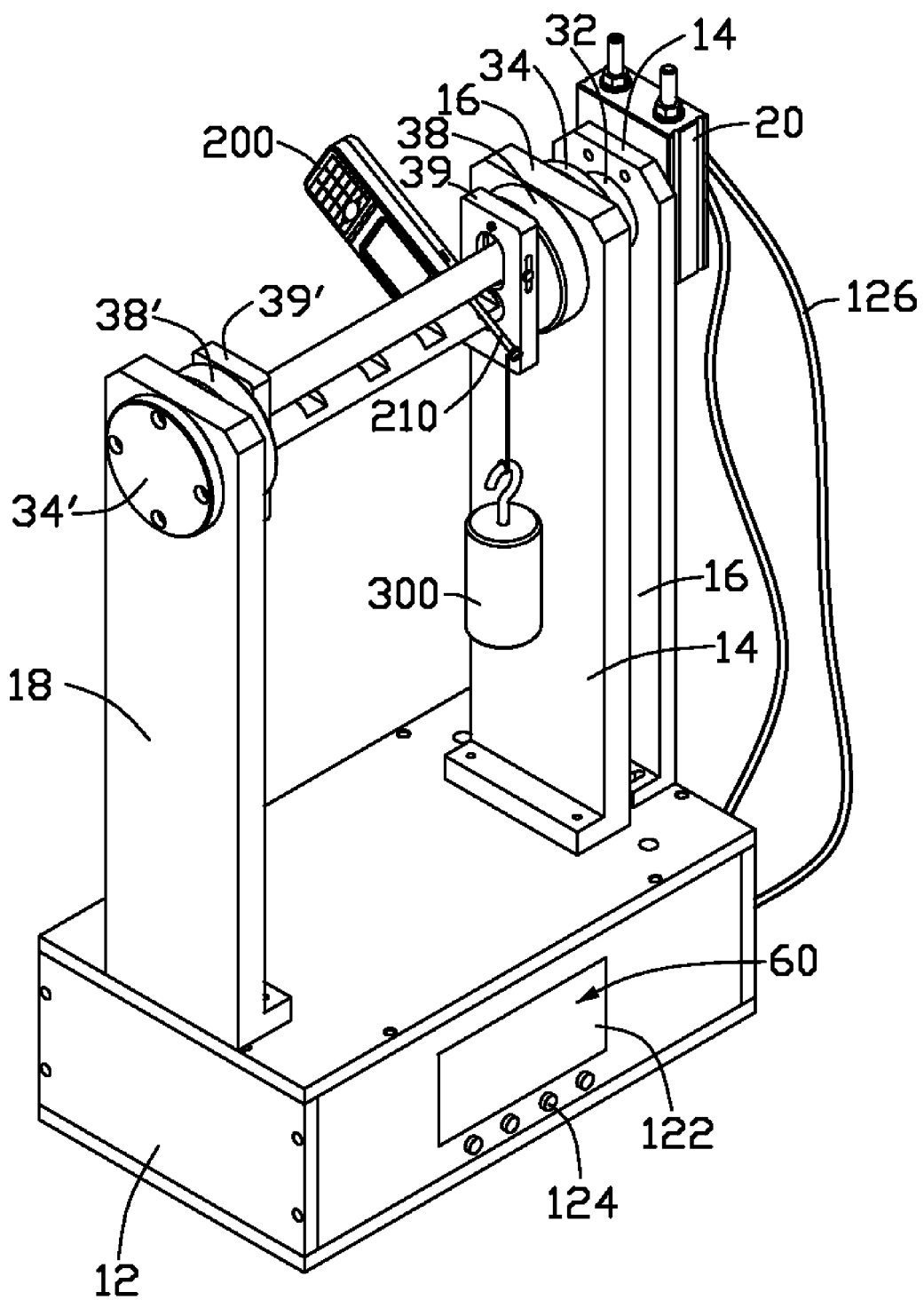
FIG. 3 is similar to FIG. 1, but showing an antenna of a mobile phone during a test.

Referring to FIG. 3, in use, an antenna 210 of a mobile phone 200 is used as an example. The screws 399 are released. The antenna 210 is inserted into and extends out from the space room between a pair of corresponding recesses 422 of the holding posts 42,44, with the main body 342 positioned at one side of the holding posts 42,44. A weight 300 is positioned at another side of the holding posts 42,44, and is fastened to a free end of the antenna 210 by a line. The screws 399 are screwed tightly so as to firmly fasten the second holding post 44. The antenna 210 is clamped by the two holding posts 42,44. The angle, speed and times of rotation of the drive shaft 24 are predetermined by the buttons 124 on the base 12. The swing blocks 39,39' are drive to rotate with the drive shaft 24 by the connecting members 38,38'. The antenna 210 bends and then rebounds to original shape at every rotation of the swing blocks 39,39' until the antenna 210 breaks. It should be understood that the force given on the antenna 210 is the same at every time of rotation, which makes the test result more precise. The times that the drive shaft 24 has rotated is shown in the display 122 in time. Thus, it could show how many times before the antenna 210 breaks.

It is to be understood that the third supporting arm 18 and the second connecting module 50 may be omitted, and the two holding posts 42,44 become shorter.

It is to be further understood that the connecting shaft 32 may be omitted, and the locking slot 324 is defined in the drive shaft 24, so that the first connecting member 38 can directly connect the drive shaft 24 by engagement of the protrusion 386 of the first connecting member 38 and the locking slot 324 of the drive shaft 24.

It is to be further understood that the second supporting arm 16, the connecting shaft 32 and the first cover 34 may be omitted, and the driving mechanism 20 is fixed to the first supporting arm 14, wherein the shaft portion 382 of the first connecting member 38 becomes shorter, the drive shaft 24 is received in the through hole 142 of the first supporting arm 14, and firmly connects with the shaft portion 382 of the connecting member.

It is to be further understood that even though numerous characteristics and advantages of the present embodiments have been set forth in the foregoing description, together with details of the structures and functions of the embodiments, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A fatigue testing apparatus comprising:
    a supporting module including a first supporting arm, the first supporting arm defining a through hole;
    a driving mechanism fixed to the supporting module, the driving mechanism being positioned at one side of the first supporting arm and having a drive shaft;
    a connecting module positioned at another side of the first supporting arm, the connecting module including a connecting member and a swing block, the connecting member passing the through hole of the first supporting arm and connecting the swing block and the drive shaft, the swing block being rotated with the drive shaft by the connecting member;
    a first holding post, one end of the first holding post being fixed to the swing block;
    a second holding post, one end of the second holding post being fixed to the swing block, the first holding post and the second holding post together clamping an element to be fatigue tested; and
    a computer system electronically connecting with the driving mechanism, the computer system controlling the rotation angle and rotation speed of the drive shaft, a display electronically connecting with the computer system, times that the drive shaft has rotated being shown by the display.

2. The fatigue test apparatus as claimed in claim 1, wherein the supporting module further comprises a base, the computer system is received in the base, and one end of the first supporting arm is fixed on the base.

3. The fatigue test apparatus as claimed in claim 2, wherein the computer system includes a plurality of buttons configured for adjusting the rotation speed and rotation angle of the drive shaft, the display and the buttons are fixed on a side wall of the base.

4. The fatigue test apparatus as claimed in claim 2, wherein the supporting module further comprises a second supporting arm, the supporting arm defines a fixing hole, the driving mechanism is fixed to the second supporting arm, and the drive shaft is received in the fixing hole.

5. The fatigue test apparatus as claimed in claim 4, wherein the connecting module further comprises a bearing, and the bearing is fixed in the through hole of the first supporting arm.

6. The fatigue test apparatus as claimed in claim 5, wherein the connecting member further comprises a connecting shaft connecting the drive shaft and the connecting member.

7. The fatigue test apparatus as claimed in claim 6, wherein the drive shaft defines a locking slot, the connecting member includes a shaft portion, and a protrusion is formed at an end of the shaft portion, engaging with the locking slot.

8. The fatigue test apparatus as claimed in claim 7, the connecting module further comprises a cover positioned between the bearing and the connecting shaft, the cover is fixed to the first supporting arm, the cover defines a shaft hole allowing the shaft portion of the connecting member to pass, the cover has a circular flange, the circular flange is received in the through hole of the first supporting arm and resisting the bearing.

9. The fatigue test apparatus as claimed in claim 6, wherein the connecting member further comprises a flange head at another end of the shaft portion, the flange head resists the bearing, and the swing block is firmly fixed to the flange head.

10. The fatigue test apparatus as claimed in claim 1, the swing block defines a holding hole and a sliding groove, one end of the first holding post is secured in the holding hole, and one end of the second holding post is slidably received in the sliding groove.

11. The fatigue test apparatus as claimed in claim 10, wherein each of the holding posts defines a plurality of recess, and each pair of corresponding recesses is configured for holding the thin element.

12. The fatigue test apparatus as claimed in claim 11, wherein the swing block defines a screw receiving hole in a sidewall thereof, the second holding post defines a positioning hole at one end thereof, and the second holding post is positioned by rotating a screw into the screw receiving hole and the positioning hole.

13. A fatigue testing apparatus comprising:
  a supporting module including defining two through holes and a fixing hole, the axes of the through holes and the fixing hole overlapping;
  a driving mechanism fixed to the supporting module, the driving mechanism having a drive shaft received in the fixing hole;
  a first connecting module fixed to one side of the supporting module and connecting the driving shaft;
  a second connecting module fixed to another side of the supporting module;
  a first holding post, one end of which fixed to the first connecting module, another end of which fixed to the second connecting module;
  a second holding post, one end of which fixed to the first connecting module, another end of which fixed to the second connecting module, the first holding post and the second holding post together clamping an element to be fatigue tested;
  a weight fastened at one end of the element to be fatigue tested; and
  a computer system electronically connecting with the driving mechanism, the computer controlling the rotation angle and rotation speed of the drive shaft, the first and second holding posts being driving to rotate by the first and second connecting module, the amount of time that the drive shaft has rotated being shown by a display of the computer system.

14. The fatigue test apparatus as claimed in claim 13, wherein the supporting module comprises a first supporting arm, a second supporting arm and a third supporting arm, the first supporting arm is positioned between the second and third supporting arm, the two through holes are respectively defined in the first supporting arm and the third supporting arm, the fixing hole is defined in the second supporting arm.

15. The fatigue test apparatus as claimed in claim 14, wherein the first connecting module is fixed to the first supporting arm and comprises a first swing block and a first connecting member, the first swing block connects the first and second holding posts, the connecting member includes a shaft portion and a flange head at one end of the shaft portion, the swing block is fixed to the first connecting member, the shaft portion passes the through hole of the first supporting hole and connects with the drive shaft.

16. The fatigue test apparatus as claimed in claim 15, wherein the first connecting module further comprises a bearing received in the through hole of the first supporting arm, the flange head of the first connecting member resists the bearing, and the rearing supports the shaft portion of the first connecting member.

17. The fatigue test apparatus as claimed in claim 16, wherein the first connecting module further comprises a connecting shaft connecting with the drive shaft, the connecting shaft defines a locking slot, the shaft portion of the first connecting member has a protrusion at another end thereof, and the protrusion is engaged in the locking slot.

18. The fatigue test apparatus as claimed in claim 17, wherein the first connecting module further comprises a cover fixed to the first supporting arm, the cover is positioned between the bearing and the connecting shaft, and the cover defines a shaft hole allowing the shaft portion of the first connecting member to pass.

19. The fatigue test apparatus as claimed in claim 14, wherein the second connecting module is fixed to the third supporting arm and comprises a second cover, a second connecting member, a second bearing and a swing block, the cover is fixed to the third supporting arm, the second bearing is received in the through hole of the third supporting hole, the second connecting member has a shaft portion receiving in the bearing and connects with the second swing block, the second swing block connects the first and second holding posts.

20. The fatigue test apparatus as claimed in claim 19, wherein each of the first and second swing blocks defines a screw receiving hole in a sidewall thereof, the second holding post defines a positioning hole at each end thereof, and the second holding post is positioned by rotating a screw into the screw receiving hole and the corresponding positioning hole.

* * * * *

UNITED STATES PATENT AND TRADEMARK OFFICE
CERTIFICATE OF CORRECTION

PATENT NO.       : 7,966,891 B2
APPLICATION NO.  : 12/417764
DATED            : June 28, 2011
INVENTOR(S)      : Lei Li et al.

It is certified that error appears in the above-identified patent and that said Letters Patent is hereby corrected as shown below:

On the title page, item (73) should read:

-- (73) Assignees:   Shenzhen Futaihong Precision Industry Co., Ltd., Shenzhen, Guangdong Province (CN); FIH (Hong Kong) Limited, Kowloon (HK) --.

Signed and Sealed this
Fourteenth Day of February, 2012

David J. Kappos
*Director of the United States Patent and Trademark Office*